US008800351B2

(12) United States Patent
Günther et al.

(10) Patent No.: US 8,800,351 B2
(45) Date of Patent: Aug. 12, 2014

(54) APPARATUS FOR TREATING A MEDICAL LIQUID, AND METHOD FOR CHECKING THE LEAKTIGHTNESS OF THE APPARATUS

(75) Inventors: Götz Günther, Oberursel (DE); Andrea Günther, legal representative, Oberursel (DE); Gesa Günther, legal representative, Stuttgart (DE); Richard Günther, legal representative, Stuttgart (DE); Ralf Müller, Bad Homburg (DE); Peter Scheunert, Friedrichsdorf (DE); Daniel Gerlach, Frankfurt am Main (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 52 days.

(21) Appl. No.: 13/133,789

(22) PCT Filed: Dec. 11, 2009

(86) PCT No.: PCT/EP2009/008881

§ 371 (c)(1), (2), (4) Date: Jun. 9, 2011

(87) PCT Pub. No.: WO2010/066441

PCT Pub. Date: Jun. 17, 2010

(65) Prior Publication Data

US 2011/0239742 A1 Oct. 6, 2011

(30) Foreign Application Priority Data

Dec. 12, 2008 (DE) ........................ 10 2008 062 037

(51) Int. Cl.
*G01M 3/04* (2006.01)

(52) U.S. Cl.
USPC ........................................................... 73/40

(58) Field of Classification Search
CPC ... A61M 1/14; A61M 1/28; A61M 2205/112; A61M 2205/70; G01M 3/3236; G01M 3/2815; G01N 15/0826
USPC ...................................... 73/37.5, 40, 46, 715
See application file for complete search history.

(56) References Cited

U.S. PATENT DOCUMENTS 7,503,915 B2 3/2009 Beden et al.
7,648,627 B2 1/2010 Beden et al.

(Continued)

FOREIGN PATENT DOCUMENTS

CN 101079387 11/2007
DE 101 57 924 C1 6/2003

(Continued)

*Primary Examiner* — Hezron E Williams
*Assistant Examiner* — David Z Huang
(74) *Attorney, Agent, or Firm* — Jacobson Holman, PLLC.

(57) ABSTRACT

An apparatus for treating a medical liquid includes a treatment machine having a coupling surface and a flexible mat arranged on the coupling surface, with a cassette made of a hard part having liquid-conducting passages therein which are covered by a flexible film that is couplable to the coupling surface of the treatment machine via the flexible mat. The apparatus includes an element for monitoring a fault-free coupling to the cassette at the coupling surface by determining a difference of the pressure between the cassette and the flexible mat and the pressure between the flexible mat and the coupling surface. A method for checking the leak tightness of the fault-free coupling employs the apparatus.

20 Claims, 1 Drawing Sheet

18 36 P1 22 44 P2 14 42 46

(56) References Cited

U.S. PATENT DOCUMENTS

| | | | | |
|---|---|---|---|---|
| 2003/0100882 | A1 | 5/2003 | Beden et al. | |
| 2003/0110832 | A1 * | 6/2003 | Carey et al. | 73/40 |
| 2005/0126998 | A1 | 6/2005 | Childers | |
| 2005/0209563 | A1 | 9/2005 | Hopping et al. | |
| 2007/0072321 | A1 * | 3/2007 | Sherrer et al. | 438/26 |
| 2009/0012454 | A1 | 1/2009 | Childers | |
| 2010/0200486 | A1 | 8/2010 | Gunther et al. | |
| 2011/0079893 | A1 | 4/2011 | Sherrer et al. | |

FOREIGN PATENT DOCUMENTS

| | | | |
|---|---|---|---|
| DE | 102 24 750 | A1 | 12/2003 |
| DE | 10 2007 042 964 | A1 | 3/2009 |
| WO | WO 2007/112512 | | 10/2007 |
| WO | WO 2007112512 | A1 * | 10/2007 |

* cited by examiner

Prior art
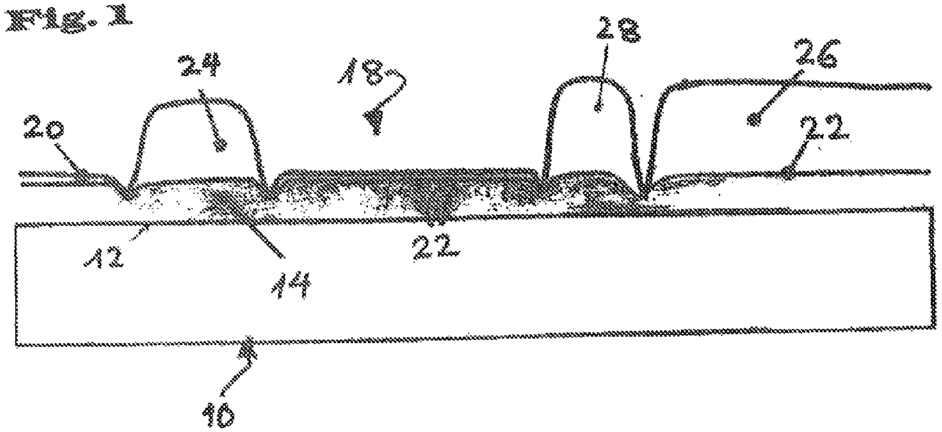
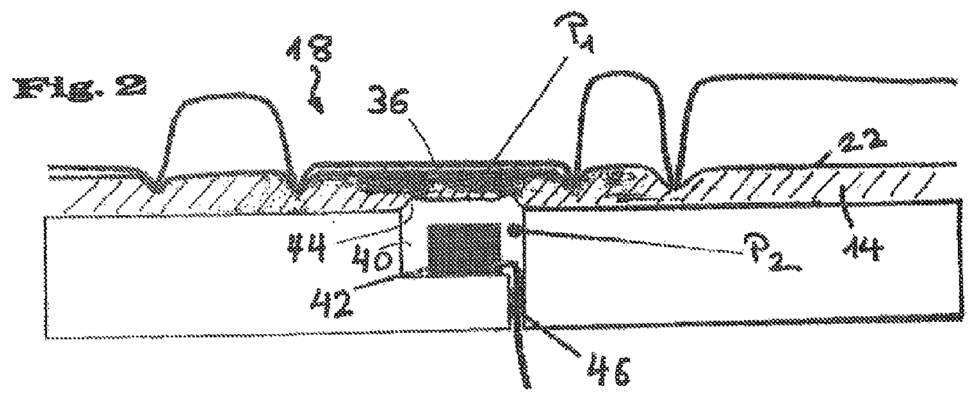
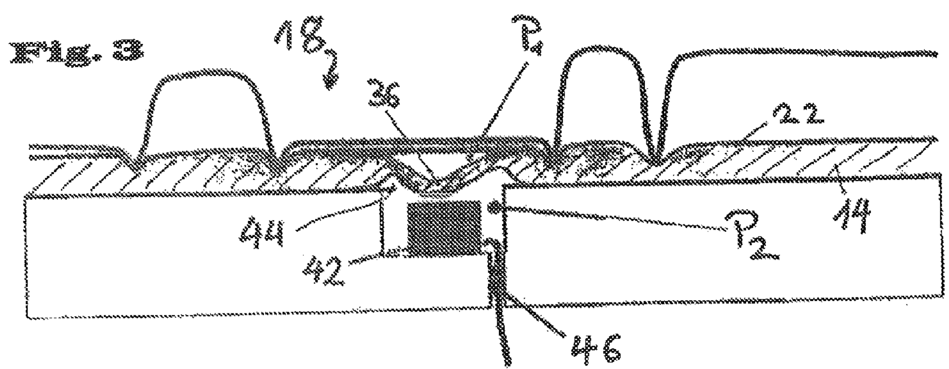

APPARATUS FOR TREATING A MEDICAL LIQUID, AND METHOD FOR CHECKING THE LEAKTIGHTNESS OF THE APPARATUS

CROSS-REFERENCE TO RELATED APPLICATIONS

This is a national stage of PCT/EP09/008881 filed Dec. 11, 2009 and published in German, which claims the priority of German number 10 2008 062 037.8 filed Dec. 12, 2008, hereby incorporated by reference.

BACKGROUND OF THE INVENTION

1. Field of Invention

The invention relates to an apparatus for the treatment of a medical liquid. The apparatus includes a treatment machine having a coupling surface and a flexible mat arranged on the coupling surface, and a cassette made from a hard material, the cassette including liquid conducting passages which are covered by a flexible film that is couplable to the coupling surface of the treatment machine via the flexible mat. The apparatus also includes suction openings in the cassette that facilitate a removal via suction of air from between the flexible film and the flexible mat, and an element that determines deflection of the flexible mat or of parts of the flexible mat. The invention furthermore relates to a method for checking the leak tightness of the aforesaid apparatus.

2. Description of the Prior Art

A corresponding apparatus for the treatment of a medical liquid can, by way of example, be a blood treatment machine such as is used in hemodialysis or in peritoneal dialysis. In such a use, the medical cassette includes the blood-conducting or dialysis liquid-conducting passages and is in communication with actuators and sensors of the treatment machine via the coupling surface. The medical cassette can thus be configured as a cost-effective disposable part, whereas the actuators for the control of the liquid flow through the cassette and the sensors are integrated into the treatment machine for the level detection or for the pressure measurement.

Such medical cassettes configured as disposable articles comprise in this connection a thin-walled three-dimensional hard plastic part having a planar peripheral contact edge and various recesses (chambers, webs and passages). Medical liquids such as dialysate or blood can now be conducted in the chambers and passages formed by these three-dimensional structures of the hard plastic part. The contact plane of the cassette is closed in a liquid tight manner by a flexible film, advantageously a polymer film which is peripherally connected, in particular welded and/or adhesively bonded, to the contact edge of the hard part. The medical cassette is pressed onto the coupling surface of the treatment machine in use with the flexible film so that actuators and sensors of the treatment machine lie on the polymer film. In addition, the flexible film is pressed together with the webs of the cassette by this pressing and thus provides a fluid tight separation of the liquid-conducting passages in the hard part by the webs and the flexible film.

Furthermore, the cassette passages can also be welded or adhesively bonded to the flexible film to achieve a fluid-tight separation of the liquid-conducting passages.

The coupling surface of the treatment machine accordingly usually has actuators, sensors and pressing force transmission surfaces. The actuators and sensors of the blood treatment machine are arranged in this context in the coupled state of the cassette opposite the liquid-conducting passages of the cassette. The actuators can hereby form valves by the pressing down of the film in that the flexible film is pressed into regions of the liquid-conducting passages and closes them. The sensors, for example, measure the pressure or temperature of the liquid located in the liquid-conducting passages. In an embodiment of the cassette, the pressing force transmission surfaces can press the flexible film against sealing webs of the hard part which surround the liquid-conducting passages to seal them with respect to one another and with respect to the rest of the cassette. Alternatively, the cassette passages can also be welded or adhesively bonded. The coupling surface is usually formed by a planar surface of a support member which is made e.g. from metal, with receivers for the sensors and the actuators being provided in said surface, and by the sensors inserted into these receivers in planar fashion.

A flexible mat, made, for example, of silicone or another elastomeric material, is usually arranged on the coupling surface of the treatment machine. This has the advantage that the sensor surfaces are protected against environmental influences and the machine surface is moreover liquid tight and thus ideally hygienically cleanable. The flexible mat in this context represents a part of the treatment machine to which the cassette is coupled as a disposable part. The operation of the actuators is ensured by the flexibility of the mat. In addition, the flexible film can be pressed well to the coupling surface via the flexible mat, whereby a good contact with the actuators, sensors and pressing force transmission surfaces is made possible.

On the coupling of the sensors to the film surface, there is the difficulty with known surfaces of achieving a good coupling to obtain correct measured values. In particular air which is trapped in the transmission path between the flexible film and the sensor surface on the insertion of the cassettes produces a falsification of the measured results. This applies to pressure sensors (in particular on the measurement of pressures which are less than the environmental pressure), but also in level detection and likewise to actuators such as valves. Unwanted air enclosures between the outer surface of the flexible film and the mat surface of the flexible mat lying thereon should therefore be eliminated on the coupling. This usually takes place by air suction.

It is already known from DE 101 57 924 C1 and DE 102 24 750 A1 to realize the air transport by means of integrated mat passages, predetermined in a defined manner, on the rear side of the machine mat at the machine side. The air line from the surface of the flexible film through the mat to the air passages arranged on the machine side takes place locally through uninterrupted slots in the region of the mat passages. The air transport however, hereby only takes place at precisely defined points of the flexible film of the cassette at which the air is sucked off through the slots in the mat to the mat passages arranged on the machine side. These mat passages therefore have to be located in the region of the liquid-conducting passages of the cassette to ensure a good suction there, which can lead to safety problems. In this embodiment, the sensor surface is no longer ideally protected from environmental influences and is not necessarily hermetically sealed by the mat so that hygienic problems can, for example, occur.

To improve the reliable air suction and for the reliable prevention of air islands, an apparatus for the treatment of a medical liquid is proposed in DE 10 2007 042 964 A1 in which a layer of an air-permeable porous material is arranged between the flexile film and the coupling surface in the coupled state, with air being able to be sucked out areally through said layer during the coupling process and/or with a coupled cassette.

To satisfy the hygienic demands, it is necessary to manufacture a closed, liquid-tight surface without sealing points, joints or material transitions. The previously mentioned uninterrupted flexible mat, which is made of silicone rubber, serves exactly this purpose. It separates the sensors and actuators from the cassette film. Two regions which have to be evacuated for the coupling of the cassette result on the basis of this separation, namely the region between the mat and the coupling surface and, on the other hand, the region between the upper side of the mat and the cassette film. Whereas the suction at the machine side between the coupling surface and the mat side facing it is solved for the sufficiently provided air conduction passages in the aforesaid DE 10 2007 042 964 A, the coupling on the cassette side is more complex and/or expensive on the cassette side due to the high demands on the cleanability and due to the machine surface.

If, for example, an intermediate space should arise between the flexible mat and the cassette film due to air leakages from the outside, this can result in the decoupling of the actuators and in incorrect measurements of the sensors.

The reasons for a collapse of the vacuum between the flexible mat and the film of the cassette lying thereon can be insufficient sealing to the ambient air. A good air permeability between the silicone mat and the film is required on the suction of the cassette film. However, it must be interrupted in the marginal region of the cassette.

A high demand is thereby made on the sealing tightness between the film and the flexible mat so that comparatively high pressure differences can be maintained. If leaks occur due to dirt, damage, collapsed points or foreign bodies, the vacuum cannot be maintained.

In known apparatus, a suction opening with a hydrophobic membrane is provided for the suction of any air present between the film and the flexible mat. The known systems are, however, very prone to failures, with corresponding failures here not being able to be detected with known apparatus. If, for example, a closure of the hydrophobic membrane of the aforesaid suction opening arises due to liquid, it cannot be detected by the machine whether the intermediate space between the film and the flexible membrane was actually evacuated. The suction can likewise be realized by an opening in the mat 12. Leak detectors on the machine side can thereby also recognize a liquid leak when a protective device with a hydrophobic membrane is provided.

If, on the other hand, due to a kinking of the pneumatic hoses in the machine, a closure of the hose occurs, the suction process of the air from the intermediate space between the film ad the flexible mat is interrupted.

A particularly critical case which can occur in an extreme case consists of the fact that on damage to the film, blood, for example, emerges from the cassette and fills the intermediate space between the film and the flexible mat. It is here not just a question of ensuring the coupling of the sensors and actuators to the cassette, but rather also to avoid the blood loss and a potential contamination of the patient's blood.

Generally, sufficiently good suction can be ensured by the evacuation possibilities between the film and the flexible mat. In this respect, not only the suction of air is possible, but rather also that of liquids—such as blood. It can thereby be assumed on a liquid leak, precisely as with a gas leak, that the penetrating medium is conveyed up to the suction opening.

SUMMARY OF THE INVENTION

It is now the object of the present invention to further develop a generic apparatus such that a monitoring of the exact coupling between the coupling surface of the treatment machine comprising a flexible mat, on the one hand, and the film covering the cassette, on the other hand, is ensured in a simple manner.

This object is solved in accordance with the invention by an apparatus for treating a medical liquid which includes a treatment machine having a coupling surface and a flexible mat arranged on the coupling surface, with a cassette made of a hard part having liquid-conducting passages which are covered by a flexible film being able to be coupled to the coupling surface of the treatment machine via the flexible mat. The air present between the flexible film and the flexible mat can be sucked out via suction openings in the cassette. In an alternative embodiment, the air can also be evacuated through openings in the mat. In a further embodiment, the air is removed manually by clamping the cassette to the mat. In this process, the air is pressed out between the cassette and the mat by mechanical pressure (for example by a lever or a door seated thereon). The flexible mat can now be made more flexible in the region above the measurement device than in other regions to facilitate a deflection there by pressure differences between the pressure level at both sides of the flexible mat.

A suitable force sensor can also be used instead of a sensor which monitors the deflection or elongation of the mat. On the use of a corresponding force sensor, only negligible deflections of the mat occur in the region of the measurement chamber. The sensor namely captures the mat in the region of the measurement space and monitors the force effect onto the mat in this region.

Special embodiments of the invention result from the subordinate claims dependent on the main claim.

Accordingly, the flexible mat can be made more flexible above the measurement device in that it is made thinner than in the other regions. Due to the thinner embodiment of the mat which is flexible per se, particularly the region above the measurement device can be deflected further and its deflection can thus be easily detected. Any differential pressure of the adjacent evacuated spaces can hereby be monitored in a simple and secure manner. Alternatively, the flexible mat can also be encompassed above the measurement device by an annular groove which likewise facilitates a deflection of the mat in the region above the measurement device.

The monitoring of the deflection of the region of the flexible mat above the measurement device is advantageously carried out by a sensor.

The sensor can advantageously be a stylus or also a sensor operating in a contactless manner such as an ultrasonic sensor, a capacitive sensor or also a light barrier. The sensor can equally be a force sensor or a pressure sensor or similar. These sensors provide the advantage that only negligibly small deflections of the mat above the measurement device are necessary for the detection of the pressure difference between the adjacent evacuated spaces.

A method in accordance with the invention for the checking of the leak tightness of the apparatus in accordance with one of the preceding claims according to the steps:

Initial checking of the measurement device before the coupling of the cassette by evacuation of the intermediate space between the mat and the coupling surface;

Coupling the medical cassette to the coupling surface of the treatment machine via a flexible mat arranged on the coupling surface; and Suction of air between the flexible film and the flexible mat during the coupling process and/or with a coupled cassette consists of the fact that the vacuum formed between the flexible film and the coupling surface is checked by a comparison of the pressure between the flexible mat and the film, on the one hand, with the pressure between the flexible mat and the coupling surface, on the other hand.

The first step of the aforesaid method sequence relates to the initial check of the measurement device. This initial check is a test of the sensor apparatus before the coupling of the cassette. The air between the mat and the coupling surface is evacuated here. This is done through a suction opening in the coupling surface. Corresponding suction passages provide a full-area evacuation of the air between the coupling surface and the mat. With a flexible embodiment, the mat moves in the direction of the sensor which monitors the elongation of the mat due to the pressure gradients which hereby arise between the sensor space and the outside air. Alternatively, on the use of a force sensor, a force here acts on the alternatively provided force sensor. A corresponding signal must therefore be recognized during the self-test to be able to confirm the problem-free function of the measurement device.

The deflection of the flexible mat above a sensor is measured for the determination of the differential pressure.

BRIEF DESCRIPTION OF THE DRAWINGS

Further features, details and advantages of the invention will be explained with reference to an embodiment shown in the drawing. There are shown:

FIG. 1: the principle structure of a cassette coupled to a treatment machine in partial section in accordance with the prior art;

FIG. 2: an embodiment of the apparatus made in accordance with the invention for the treatment of the medical liquid in a first working position; and FIG. 3: the apparatus in accordance with FIG. 2 in a second working position.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 shows an apparatus for treating a medical liquid such as is used in the prior art, for example for hemodialysis or peritoneal dialysis. Such apparatus can, however, also be used in a plurality of other fields of application in which a disposable cassette, which is also called a disposable, is used and is coupled to sensors and actuators of a treatment machine via a coupling surface.

The treatment surface 10 in this connection has a coupling surface 12 and a flexible mat 14 arranged on the coupling surface 12. A cassette 18 encompasses a hard part 20 as well as a flexible film 22; different blood passages 24, 26, 28 are defined by the hard part 20 and/or the flexible film 22.

In accordance with the exemplary embodiment of the invention shown in FIGS. 2 and 3, the monitoring of the vacuum between the film 22 and the flexible mat 14 is now realized by a comparison of the pressure on the machine side with the pressure between the flexible mat 14 and the coupling surface 12 with the pressure between the film 22 and the flexible mat 14. For this purpose, as is shown in FIGS. 2 and 3, the region 36 of the flexible mat 14 above a sensor 42 is preferably made thinner than in its other regions and is thereby made more flexible and more yielding. After the initial test, the air between the flexible mat and the coupling surface 12 is evacuated. The part of the flexible mat which is located above the sensor 42 is accordingly moved in the direction of the sensor by the external pressure. With a correct coupling of the cassette 18 to the mat 14, the air between the cassette 18 and the mat 14 is evacuated. The pressure difference between the pressures P1 in the space between the cassette 18 and the mat 14 and P2 in the space between the mat 14 and the coupling surface 12 is accordingly zero. No outer forces thus act onto the partial piece (i.e., region) 36 of the flexible mat above the sensor and the mat adopts its previously flat shape in this region, as shown in FIG. 2.

In FIG. 3, the case is shown that the coupling of the cassette 18 to the mat 14 has not taken place properly, that is, the air between the cassette 18 and the mat 14 was not completely removed. The pressure P1 in the space between the cassette 18 and the mat 14 is thus larger than the pressure P2 in the space between the mat 14 and the coupling surface 12, whereby the region 36 of the flexible mat above the sensor remains arched in the direction of the sensor.

The sensor 42 detects the deflection of the flexible mat above the sensor in a suitable manner. This sensor can, for example, comprise a contactless sensor such as an ultrasonic sensor or a capacitive sensor. Instead of the sensor 42 shown here, a reflected light barrier can, for example, also be used which is completely covered in the region of the more flexibly designed region 36 on the deflection of the flexible mat 14.

A flexible annular groove 44 is provided, as shown in FIGS. 2 and 3, for the improvement of the deflection of the region 36 of the flexible mat 14 made thinner.

In an alternative embodiment, the partial piece 36 of the flexible mat 14 is preshaped in the direction of the sensor 42. In this respect, the situation results as shown in FIG. 3 without any evacuation of the air between the flexible mat 14 and the coupling surface 12. With a correct coupling of the cassette 18 to the mat 14, the air between the cassette 18 and the mat 14 is evacuated. The pressure P1 in the space between the cassette 18 and the mat 14 is accordingly smaller than the pressure P2 in the space between the mat 14 and the coupling surface. A force thus acts onto the partial piece 36 of the flexible mat above the sensor away from the sensor 42, whereby the partial piece 36 of the flexible mat 14 is pressed toward the cassette 18, as shown in FIG. 2. The proper coupling of the cassette 18 to the mat 14 is also monitored in this embodiment by measurement of the deflection of the partial piece 36 of the flexible mat 14 by a suitable sensor.

If now, as shown in the example of FIG. 3, it is found that the vacuum between the film 22 and the flexible mat 14 was not maintained, a previously determined measure can be initiated such as the ending of the treatment to guard against a risk to the patient. For this purpose, the signal of the sensor 42 is forwarded in a previously unknown manner via the line 46 to a control device not shown in any more detail here and in which, after the arrival of the corresponding signal, suitable measures were taken to terminate the treatment.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for the treatment of a medical liquid comprising:

a treatment machine having a coupling surface and a flexible mat arranged on the coupling surface, a disposable cassette couplable to said treatment machine, having a hard material of construction and including liquid conducting passages which are covered by a flexible film that is couplable to the coupling surface of the treatment machine via the flexible mat, with air between the flexible film and the flexible mat being removable in order to provide a vacuum therebetween, a measurement chamber arranged in the coupling surface, and a sensor arranged in the measurement chamber, the sensor being configured to detect a deflection of a region of the flexible mat disposed above the measurement chamber, the deflection resulting from a differential pressure between (i) a pressure in an area between the flexible mat and the flexible film, and (ii) a pressure in the measurement chamber.

2. The apparatus in accordance with claim 1, wherein the flexible mat is configured to be more flexible in the region disposed above the measurement chamber than in other regions thereof.

3. The apparatus in accordance with claim 1, wherein the flexible mat is more flexible in the region disposed above the measurement chamber by being thinner at said region disposed above the measurement chamber than in other regions thereof.

4. The apparatus in accordance with claim 1, wherein the region of the flexible mat disposed above the measurement chamber is encompassed by an annular groove.

5. The apparatus in accordance with claim 1, wherein the region of the flexible mat disposed above the measurement chamber has a curved form that is preshaped in a direction toward the sensor.

6. The apparatus in accordance with claim 1, wherein the sensor is a push-button switch.

7. The apparatus in accordance with claim 1, wherein the sensor operates in a contactless manner.

8. The apparatus in accordance with claim 7, wherein the sensor is an ultrasonic sensor, a capacitive sensor, or a light barrier.

9. The apparatus in accordance with claim 1, wherein the sensor is a pressure sensor or a force sensor.

10. A method of assessing the leak tightness of the apparatus in accordance with claim 1, said method comprising the following steps:

coupling the disposable cassette to the coupling surface of the treatment machine via the flexible mat arranged on the coupling surface, suctioning the air from between the flexible film and the flexible mat during the coupling and/or with a coupled disposable cassette to provide the vacuum therebetween, detecting the deflection of the region of the flexible mat disposed above the measurement chamber that results from the differential pressure, and assessing the vacuum created between the flexible film and the flexible mat based on the deflection, with a deflection of the flexible mat in a direction of the sensor indicating that the vacuum is not present.

11. The method in accordance with claim 10, further comprising, before the step of coupling the disposable cassette, a step of evacuating an intermediate space between the flexible mat and the coupling surface, including the measurement chamber, so as to perform an initial assessment of the sensor.

12. A treatment machine to which a disposable cassette is couplable for the treatment of a medical liquid, said disposable cassette having a hard material of construction, and including liquid conducting passages which are covered by a flexible film that is couplable to a coupling surface of the treatment machine via a flexible mat, with air between the flexible film and the flexible mat being removable in order to provide a vacuum therebetween, said treatment machine comrising:

a coupling surface and a flexible mat arranged on the coupling surface, a measurement chamber arranged in the coupling surface, and a sensor arranged in the measurement chamber, the sensor being configured to detect a deflection of a region of the flexible mat disposed. above the measurement chamber, the deflection resulting from a differential pressure between (i) a pressure in an area between the flexible mat and the flexible film, and (ii) a pressure in the measurement chamber.

13. The treatment machine according to claim 12, wherein the flexible mat is configured to be more flexible in the region disposed above the measurement chamber than in other regions thereof.

14. The treatment machine according to claim 12, wherein the flexible mat is more flexible in the region disposed above the measurement chamber by being thinner at said region disposed above the measurement chamber than in other regions thereof.

15. The treatment machine according to claim 12, wherein the region of the flexible mat disposed above the measurement chamber is encompassed by an annular groove.

16. The treatment machine according to claim 12, wherein the region of the flexible mat disposed above the measurement chamber has a curved form that is preshaped in a direction toward the sensor.

17. A disposable cassette couplable to a machine for the treatment of a medical liquid, said machine having a coupling surface and a flexible mat arranged on the coupling surface, a measurement chamber arranced in the coupling surface, and a sensor arranged in the measurement chamber, the sensor being configured to detect a deflection of a region of the flexible mat disposed above the measurement chamber, the deflection resulting from a differential pressure between the disposable cassette and the treatment machine, said disposable cassette comprising:

a thin-walled three-dimensional part having a hard material of construction, and liquid conducting passages covered by a flexible film that is couplable to the coupling surface of the treatment machine via the flexible mat, with the disposable cassette being configured such that air between the flexible film and the flexible mat is removable in order to provide a vacuum-based coupling of the disposable cassette.

18. The disposable cassette according to claim 17, wherein a contact plane of the disposable cassette is closed in a liquid-tight manner by the flexible film.

19. The disposable cassette according to claim 17, wherein the flexible film has a material of construction that is a polymer, and is peripherally connected to a contact edge of the three-dimensional part.

20. The disposable cassette according to claim 19, wherein a connection of the flexible film to the contact edge is via a weld or an adhesive bond.

* * * * *